US012654021B2

(12) United States Patent
Calderon et al.

(10) Patent No.: US 12,654,021 B2
(45) Date of Patent: Jun. 16, 2026

(54) IMPLANTABLE MEDICAL DEVICE CHARGERS AND CHARGER POSITIONING SUPPORTS FOR USE WITH SAME

(71) Applicant: The Alfred E. Mann Foundation for Scientific Research, Valencia, CA (US)

(72) Inventors: Joseph L. Calderon, Santa Clarita, CA (US); Edward Hillery, Valencia, CA (US); Susanna M. Lin, Los Angeles, CA (US)

(73) Assignee: The Alfred E. Mann Foundation for Scientific Research, Valencia, CA (US)

( * ) Notice: Subject to any disclaimer, the term of this patent is extended or adjusted under 35 U.S.C. 154(b) by 762 days.

(21) Appl. No.: 18/175,522

(22) Filed: Feb. 27, 2023

(65) Prior Publication Data

US 2023/0293896 A1     Sep. 21, 2023

Related U.S. Application Data

(60) Provisional application No. 63/322,170, filed on Mar. 21, 2022.

(51) Int. Cl.
 A61N 1/378          (2006.01)
 H02J 7/00            (2026.01)
          (Continued)

(52) U.S. Cl.
 CPC .............. A61N 1/3787 (2013.01); H02J 7/70 (2026.01); H02J 50/10 (2016.02); H02J 50/90 (2016.02)

(58) Field of Classification Search
 CPC .............. A61N 1/3787; A61N 1/37223; A61N 1/37229; H02J 7/0042; H02J 50/10; H02J 50/90; H01F 27/02; H01F 38/14
          (Continued)

(56) References Cited

U.S. PATENT DOCUMENTS 8,473,066 B2 *  6/2013  Aghassian .............. H02J 50/10
                                                             607/30
9,205,273 B2 *  12/2015  Dearden ............ A61N 1/36125
          (Continued)

FOREIGN PATENT DOCUMENTS

WO     WO-2018017346 A1 *  1/2018  ............. A61N 1/375
WO     WO 2018209836 A1    11/2018

OTHER PUBLICATIONS

C. Niu, H. Hao, L. Li, B. Ma and M. Wu, "The Transcutaneous Charger for Implanted Nerve Stimulation Device," 2006 International Conference of the IEEE Engineering in Medicine and Biology Society, New York, NY, USA, 2006, pp. 4941-4944.*
          (Continued)

*Primary Examiner* — M Baye Diao
(74) *Attorney, Agent, or Firm* — Henricks Slavin LLP

(57)                    ABSTRACT

An implantable medical device (IMD) charger apparatus may include an IMD charger including a housing defining a bottom surface, a primary coil located within the housing, and a fastener on the bottom surface of the housing, and a charger support, mounted on the IMD charger, including a bottom surface, and movable between a first state and a second state. The IMD charger and the charger support may be respectively configured such that the IMD charger fastener is above the charger support bottom surface when the charger support is in the first state and the IMD charger fastener is at or below the charger support bottom surface when the charger support is in the second state.

18 Claims, 8 Drawing Sheets

(51) Int. Cl.
    *H02J 7/70*         (2026.01)
    *H02J 50/10*       (2016.01)
    *H02J 50/90*       (2016.01)

(58) Field of Classification Search
    USPC ........................................................ 320/108
    See application file for complete search history.

(56) References Cited

U.S. PATENT DOCUMENTS

| | | | |
|---|---|---|---|
| 10,342,984 B2 * | 7/2019 | Stouffer | H01F 27/2804 |
| 11,129,996 B2 | 9/2021 | Aghassian et al. | |
| 2009/0082835 A1 * | 3/2009 | Jaax | H02J 50/10 |
| | | | 607/61 |
| 2010/0217353 A1 | 8/2010 | Forsell | |
| 2010/0331917 A1 | 12/2010 | DiGiore et al. | |
| 2011/0004278 A1 * | 1/2011 | Aghassian | H02J 50/90 |
| | | | 607/61 |
| 2011/0106210 A1 | 5/2011 | Meskens | |
| 2016/0175600 A1 | 6/2016 | Amir et al. | |
| 2016/0199657 A1 | 7/2016 | Jiang et al. | |
| 2018/0229045 A1 * | 8/2018 | McDonald | A61N 1/3787 |
| 2018/0361165 A1 * | 12/2018 | Jaax | H02J 7/007192 |
| 2020/0338357 A1 | 10/2020 | Jiang et al. | |

OTHER PUBLICATIONS

PCT International Search and Written Opinion dated May 22, 2023 for PCT App. Ser. No. PCT/US2023/063383.

\* cited by examiner

IMPLANTABLE MEDICAL DEVICE CHARGERS AND CHARGER POSITIONING SUPPORTS FOR USE WITH SAME

CROSS-REFERENCE TO RELATED APPLICATION

This application claims the benefit of U.S. Provisional Application No. 63/322,170, filed Mar. 21, 2022, an entitled "Implantable Medical Device Chargers and Charger Positioning Supports For Use With Same," which is incorporated herein by reference.

BACKGROUND OF THE INVENTIONS

1. Field of the Inventions

The present inventions relate generally to the charging of rechargeable power sources in implanted medical devices.

2. Description of the Related Art

Implantable medical devices ("IMDs") such as, for example, implantable pulse generators, vagus nerve stimulators and drug infusion pumps, frequently include therapeutic and/or diagnostic components as well as rechargeable power sources such as rechargeable batteries, capacitors, and combinations thereof. External IMD chargers (or "IMD chargers") are used to wirelessly and transcutaneously transmit power to IMDs via inductive coupling. To that end, IMD chargers include a primary charging coil and the IMDs include a secondary charging coil. The primary charging coils of the IMD chargers may be energized to create a magnetic charging field that induces current in the secondary charging coils of the IMDs. The current is used to recharge the batteries or other rechargeable power sources.

One issue associated with the use of IMDs and IMD chargers is the distance between the charging coils, which should be minimized to the extent practicable. Another issue is charging alignment. Each charging coil defines a central axis and the coils are aligned when the axes are colinear. Mis-alignment of the charging coils reduces the efficiency of the power transfer and, accordingly, some IMD chargers are configured to determine whether or not the primary and secondary charging coils are properly aligned with one another and to provide feedback, such as audible, visible and/or tactile feedback, that is indicative of whether or not the charging coils are properly aligned. Examples of IMD chargers with alignment determination and audible, visible and/or tactile feedback capabilities may be found in, for example, US Pat. Pub. No. 2013/0096651 A1 and US Pat. Pub. No. 2017/0361115 A1, which are incorporated herein by reference.

In some instances, a garment or other wearable article (collectively "wearable articles") may be used to maintain the aligned position of the IMD charger on the body relative to the IMD. The IMD charger and the wearable article in some instances include respective hook and loop portions of a hook and loop fastener (commonly sold under the tradename Velcro) that secures the IMD charger to the wearable article when the IMD charger is pressed against the wearable article. Examples of such IMD chargers and wearable articles may be found in, for example, US Pat. Pub. No. 2013/0096651 A1.

SUMMARY

The present inventors have determined that conventional IMD chargers and the manner in which the primary charging coil is aligned with the secondary charging coil of the associated IMDs, as well as the manner in which the IMD chargers are secured to the IMD recipient, are susceptible to improvement. For example, aligning the IMD charger with the IMD sometimes involves placing the IMD charger near a wearable article worn by the IMD recipient and moving the IMD charger relative to the wearable article until the primary and secondary charging coils are aligned. The present inventors have determined that positioning the IMD charger would be easier for the recipient if the IMD charger could be placed against wearable article and moved over the recipient in a sliding motion during the alignment process. The present inventors have further determined that the hook and loop fastener (or other fastener) that secures the IMD charger to the wearable article would prevent the IMD charger from sliding along the wearable article.

An implantable medical device (IMD) charger apparatus in accordance with at least one of the present inventions may include an IMD charger including a housing defining a bottom surface, a primary coil located within the housing, and a fastener on the bottom surface of the housing, and a charger support, mounted on the IMD charger, including a bottom surface, and movable between a first state and a second state. The IMD charger and the charger support may be respectively configured such that the IMD charger fastener is above the charger support bottom surface when the charger support is in the first state and the IMD charger fastener is at or below the charger support bottom surface when the charger support is in the second state.

A method in accordance with at least one of the present inventions may include positioning an IMD charger apparatus including an IMD charger with a housing defining a bottom surface, a primary coil located within the housing and a fastener on the bottom surface, and a charger support with a bottom surface, on either the IMD recipient or a wearable article worn by the IMD recipient in such a manner that the bottom surface of the charger support is in contact with the IMD recipient or the wearable article and the fastener of the IMD charger is spaced apart from the contacted IMD recipient or the wearable article, moving the IMD charger into charging alignment with an IMD within the IMD recipient while the charger support is in contact with the IMD recipient or the wearable article, and after the IMD charger has been moved into charging alignment with the IMD, pressing the IMD charger downward until the fastener of the IMD charger is in contact with the IMD recipient or the wearable article.

There are a variety of advantages associated with such apparatus and methods. By way of example, but not limitation, the apparatus and methods allow an IMD charger to be placed against the IMD recipient (or wearable article on the IMD recipient) and moved in a sliding motion during the coil alignment process without interference from the fasteners that secure the IMD charger to the IMD recipient (or wearable article on the IMD recipient).

BRIEF DESCRIPTION OF THE DRAWINGS

Detailed descriptions of exemplary embodiments will be made with reference to the accompanying drawings.

DETAILED DESCRIPTION OF THE EXEMPLARY EMBODIMENTS

Figure 2:
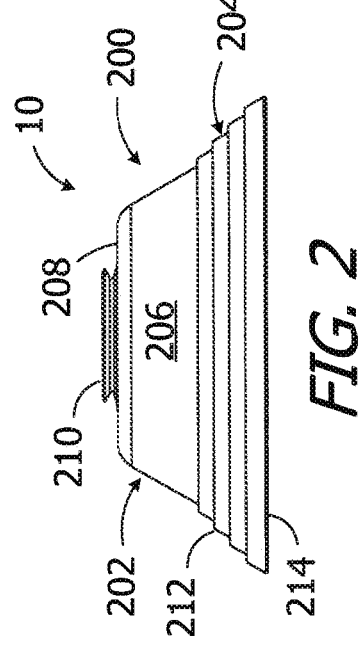
FIG. 2 is a side view of the IMD charger apparatus illustrated in FIG. 1.
Figure 4:
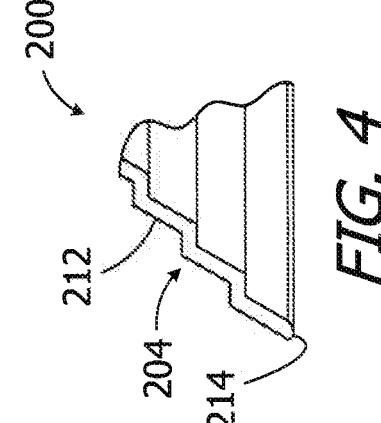
FIG. 4 is a section view of a portion of the IMD charger apparatus illustrated in FIG. 1.
Figure 1:
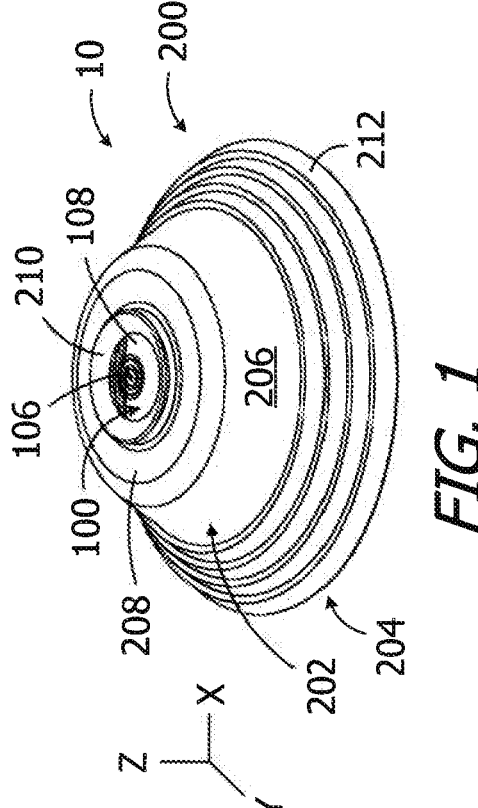
FIG. 1 is a perspective view of an implantable medical device (IMD) charger apparatus in accordance with one embodiment of a present invention in a first state.
Figure 3:
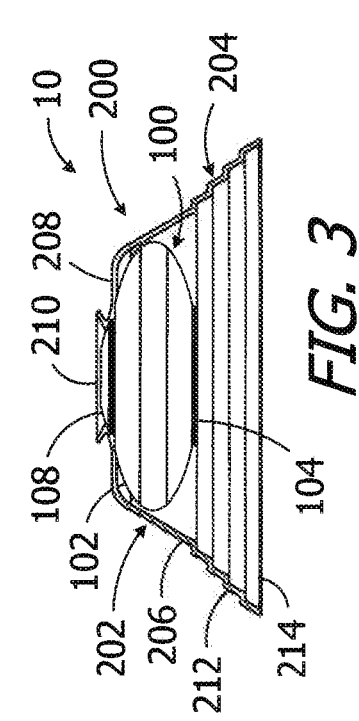
FIG. 3 is a partial section view of the IMD charger apparatus illustrated in FIG. 1.
Figure 6:
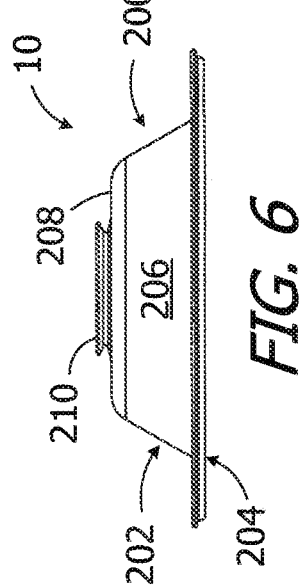
FIG. 6 is a side view of the IMD charger apparatus illustrated in FIG. 1 in the second state.
Figure 8:
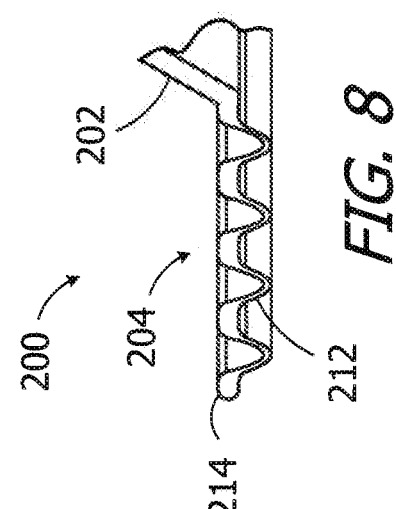
FIG. 8 is a section view of a portion of the IMD charger apparatus illustrated in FIG. 1 in the second state.
Figure 5:
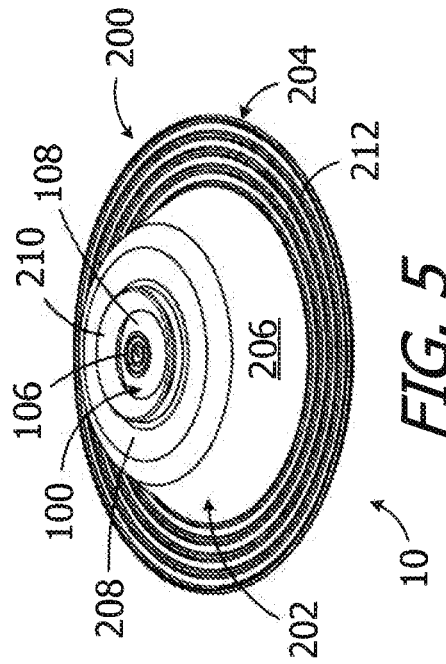
FIG. 5 is a perspective view the IMD charger apparatus illustrated in FIG. 1 in a second state.
Figure 7:
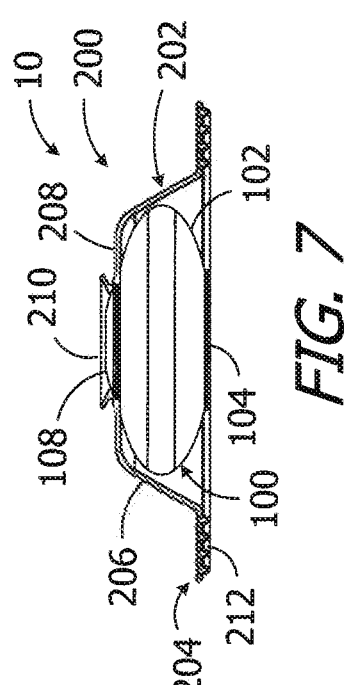
FIG. 7 is a partial section view of the IMD charger apparatus illustrated in FIG. 1 in the second state.
Figure 9:
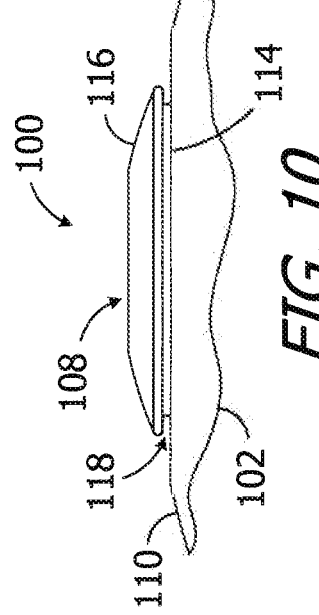
FIG. 9 is a perspective view of a portion of the IMD charger apparatus illustrated in FIG. 1.

The following is a detailed description of the best presently known modes of carrying out the inventions. This description is not to be taken in a limiting sense, but is made merely for the purpose of illustrating the general principles of the inventions.

As illustrated for example in FIGS. 1-8, an implantable medical device (IMD) charger apparatus 10 in accordance with one embodiment of a present invention includes an IMD charger 100 and a charger positioning support (or "charger support") 200 that is mounted to the IMD charger and is movable between a first (or "extended") state (FIGS. 1-4) and a second (or "compressed") state (FIGS. 5-8). As is discussed in greater detail below, the charger support 200 allows the IMD charger apparatus 10 to be placed onto a wearable article or body surface and moved laterally relative to IMD during the positioning process, i.e., along the body of the recipient in the X-Y plane (FIG. 1), and to thereafter be pressed in the Z-direction to place the IMD charger 100 against the recipient or a wearable article worn by the recipient.

Referring to FIGS. 1-4, the exemplary IMD charger 100 includes a housing 102, a fastener 104 that is associated with the bottom of the housing, a user interface 106 such as a power button, and a connector 108 that is associated with top surface of the housing and configured to mate with a corresponding connector on the charger support. As used herein, the word "bottom" refers to the portion of the IMD charger apparatus that faces the associated IMD when in use, and the word "top" refers to the portion of the IMD charger apparatus that faces away from the associated IMD when in use. Various exemplary fasteners are described below with reference to FIG. 12, while the internal components of the IMD charger 100 are described below with reference to FIG. 13A.

Figure 10:
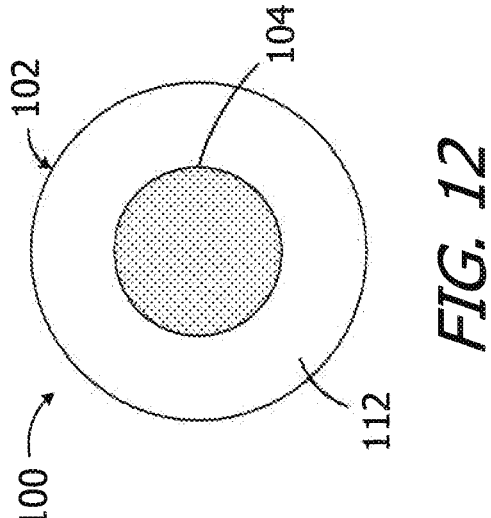
FIG. 10 is a side view of a portion of the IMD charger apparatus illustrated in FIG. 1.
Figure 11:
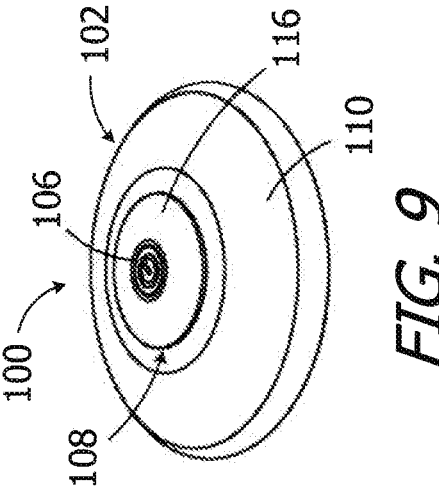
FIG. 11 is a section view of a portion of the IMD charger apparatus illustrated in FIG. 1.

The exemplary charger support 200 includes a base portion 202 and a collapsible portion 204. The base portion 202 in the exemplary implementation has a frustoconical wall 206, an annular end wall 208, and a connector 210 that is configured to mate with the charger connector 108. The connectors 108 and 210 are discussed in greater detail below with reference to FIGS. 10 and 11. The collapsible portion 204 includes a plurality of pleats 212 and a smooth, semi-circular or otherwise curved bottom end 214. The collapsible portion 204 defines a generally frustoconical shape similar to that of the base wall 206 when the charger support 200 is in the first (or "extended") state, as shown in FIGS. 1-4, and generally flat, annular shape when in the second (or "compressed") state, as shown in FIGS. 5-8. The charger support 200 may be biased to the first (or "extended") state in some implementations. The respective configurations of the IMD charger 100 and charger support 200 may be such that the fastener 104 is located above the bottom end 214 when the charger support 200 is in the first (or "extended") state and is located at or below the bottom end when the charger support is in the second (or "compressed") state. Put another way, the respective configurations of the IMD charger 100 and charger support 200 may be such that the fastener 104 cannot be fastened to, for example, a corresponding fastener worn by the IMD recipient, when the charger support 200 is in the first (or "extended") state and can be fastened to, for example, a corresponding fastener worn by the IMD recipient when the charger support is in the second (or "compressed") state.

Turning to FIGS. 9-12, the housing 102 of the exemplary IMD charger 100 includes a top portion 110 and a bottom portion 112, and the connector 108 is associated with the top portion. Although not so limited, the exemplary connector 108 includes a post 114 and a head 116 that has a larger outer perimeter than the post. A slot 118 is located between the housing upper portion 110 and the head 116. The connector 210 on the exemplary charger support 200 is configured to mate with the connector 108 and, to that end, includes receptacle 216 with a shape that corresponds to the shape of the connector 108. The receptacle 216 is defined by an inner surface portion 218, with a size and shape that corresponds to the size and shape of the post 114, and an inner surface portion 220, with a size and shape that corresponds to the size and shape of the head 216. The connector 210 may also include a handle 222 and an opening 224 to facilitate access to the user interface 106.

Charger supports (e.g., the exemplary charger support 200) may be either "removably mounted" or "permanently mounted" to the associated IMD charger (e.g., IMD charger 100). As used herein, a "removable" charger support is a charger support that will remain mounted to the associated IMD charger during usage, such as the usage described below with reference to FIGS. 15 and 16, and that may also be removed from or mounted to the IMD charger without damage to the charger support, or damage to or disassembly of the IMD charger. As used herein, a "permanently attached" charger support is a charger support that is mounted to the associated IMD charger in such a manner that removal of the charger support from the IMD charger involves damage to the charger support, or damage to or disassembly of the IMD charger.

The charger support 200 is removably mounted to the IMD charger 100 in the exemplary implementation. To that end, the charger support 200 may be formed from resilient material that allows the connector 210 to be stretched over and onto the connector 108. Suitable materials include, but are not limited to, flexible biocompatible materials (including resilient materials) such as silicone, polycarbonate, polyurethane, polysulfone, and polyamide. The flexibility of the charger support 200 also facilitates the collapsing of the charger support collapsible portion 204. The charger housing 102, as well as the connector 108, may in at least some instances be formed from a rigid material.

Figure 12:
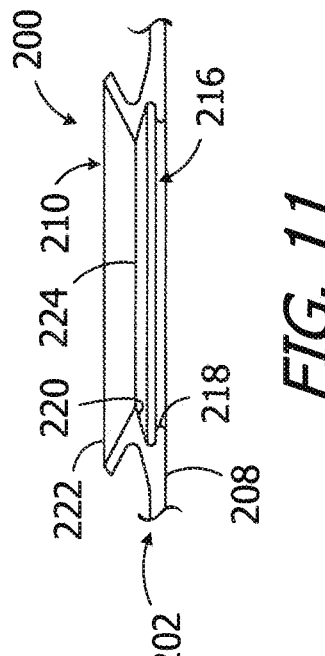
FIG. 12 is a bottom view of a portion of the IMD charger apparatus illustrated in FIG. 1.

The exemplary fastener 104 illustrated in FIG. 12 may be any device that is capable of securing an IMD charger, such as IMD charger 100, to a wearable article or to skin. By way of example, the faster 104 may be the hook (or loop) portion of a hook and loop faster apparatus which may be secured to the loop (or hook) portion that is worn by the IMD recipient. One example of a wearable article that includes the loop portion is discussed below with reference to FIGS. 14-16. IMD chargers and their associated wearable articles may also be provided with respective portions of a plurality of snaps, buttons and any other suitable fasteners. In those instances where the wearable article is merely a shirt or other garment that the IMD recipient is wearing, the recipient may be provided with, for example, a small disc with a snap post while the IMD charger may be provided with a snap receptacle. The disc may be slid under the garment after the IMD charger alignment has been confirmed, and the post and receptacle may be connected to one another with the garment sandwiched between the two. Adhesive tape, such as double-sided tape or dots, that in some instances may be appropriate for contact with the skin or a wearable article and/or removable and replaceable from the associated IMD charger may be employed.

Figures 13A, 13B:
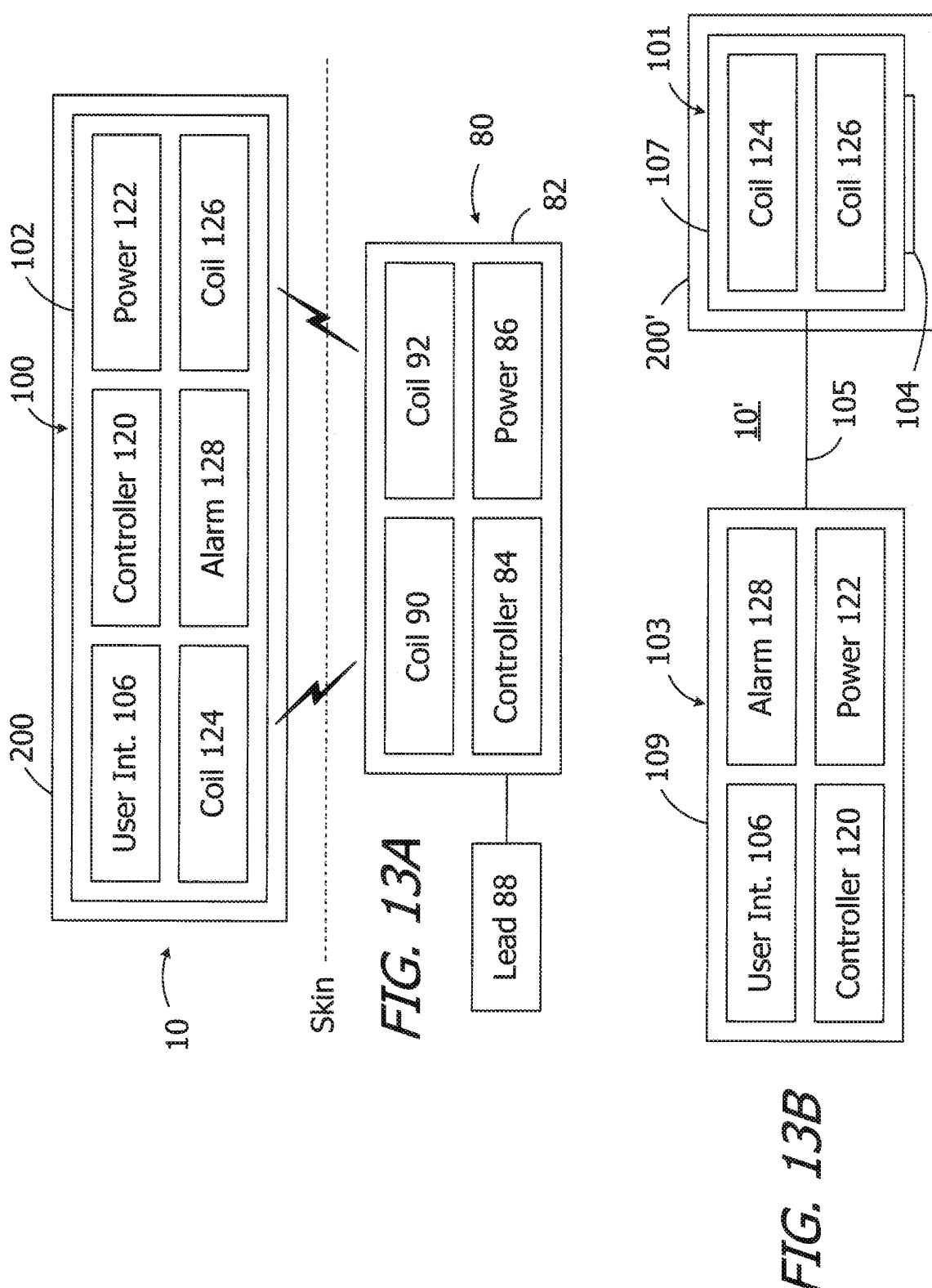
FIG. 13A is a block diagram of the IMD charger apparatus illustrated in FIG. 1 in combination with an exemplary IMD.
FIG. 13B is a block diagram of an IMD charger apparatus in accordance with one embodiment of a present invention.

Referring to FIG. 13A, and although the present inventions are not limited to any particular IMDs and IMD chargers, the exemplary IMD charger 100 may be used in conjunction with an IMD 80 (e.g., an implantable pulse generator) that includes a case 82 formed from a biocompatible material such as titanium, a controller 84, a battery or other rechargeable power source 86, and a lead 88 with a plurality of conductive contacts (not shown). Power and data transmission may be facilitated by a secondary charging coil 90, a telemetry coil 92, and associated circuitry (not shown). In addition to the aforementioned housing 102 and user interface 106, the exemplary IMD charger 100 includes a controller 120, a power source 122 (either rechargeable or replaceable), a primary charging coil 124 and a telemetry coil 126 for power and data transmission. Power and data transmission occurs transcutaneously through a recipient's skin and other tissue by way of inductive coupling. The exemplary IMD charger 100 may also include an alarm 128 that is configured to provide an audible, visible and/or tactile indication that the IMD primary charging coil 124 is aligned with IMD secondary charging coil 90, as determined by the controller 120.

It should be noted here that, in some instances, various components of IMD chargers in accordance with the present inventions may be placed into separate housings. As illustrated in FIG. 13B, the exemplary IMD charger apparatus 10' includes an IMD charger with a coil module 101 and an electronics module 103 that are connected by a cable 105, as well as a charger support 200'. The coil module 101 includes a fastener 104 and a housing 107 for the coils 124 and 126, while the electronics module 103 includes a housing 109 for the user interface 106, controller 120, power source 122 and alarm 128. Such an arrangement allows the IMD recipient to have a relatively small and light coil module 101 secured to their wearable article or body, while the larger and heavier electronic components can be placed into a pocket or worn on a belt. The charger support 200' may substantially similar to the other charger supports described herein, albeit smaller, and function in the same way.

Figures 14, 15, 16:
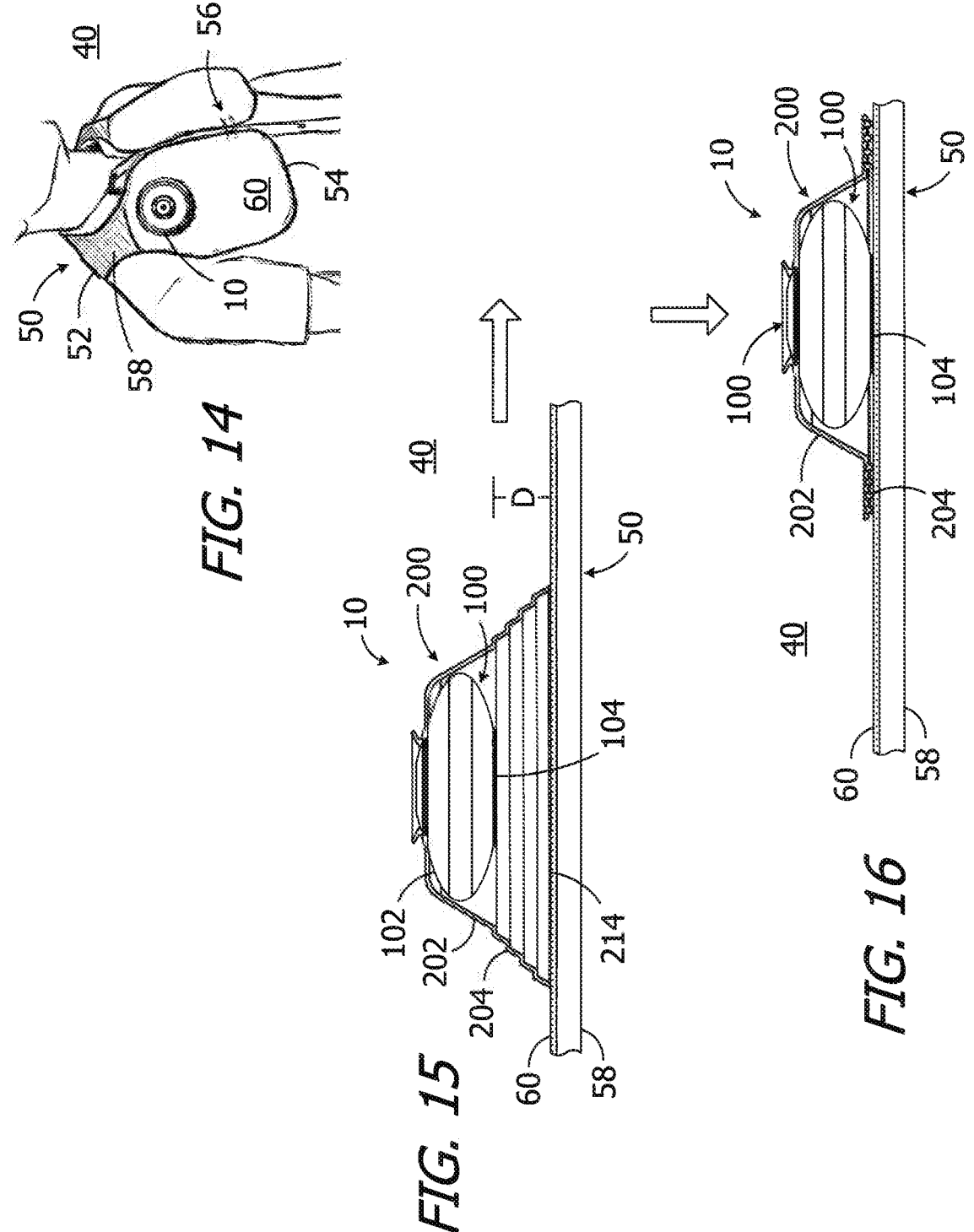
FIG. 14 is a perspective view an IMD charger system in accordance with one embodiment of a present invention.
FIG. 15 is a partial section view of the IMD charger system illustrated in FIG. 14.
FIG. 16 is a partial section view of the IMD charger system illustrated in FIG. 14.

Referring to FIG. 14, one example of a wearable article that may be used in a charging system 40 that includes the IMD charger apparatus 10, or the like, is the garment 50. The exemplary garment 50, which is configured to extend behind the recipient's neck and downwardly over the chest, includes a shoulder/neck portion 52, a pair of chest portions 54, and one or more straps 56 or other connectors that secure the chest portions to one another and maintain the respective positions of the chest portions. The garment 50 may have a base layer 58 that forms the shoulder/neck portion 52 and chest portions 54 as well as a pair of fastener layers 60 that are secured to the base layer in the chest portions. The fastener layers 60 in the illustrated implementation are the loop portion of a hook and loop fastener and are configured to mate with the fastener 104, i.e., the hook portion of the hook and loop fastener, on the IMD charger 100. In other embodiments, the base layer may be omitted from the chest portions so that the chest portions consist only of a layer of loop material. The garment 50 and other wearable articles may in at least some instances be custom fitted for the IMD recipient to reduce the likelihood of charger movement. They may also be configured to be worn on any portion of the body.

To position the IMD charger apparatus 10 over an IMD, such as IMD 80, the IMD charger apparatus may be placed against the garment 50 in such a manner that the curved bottom end 214 of the charger support 200 rests upon one of the fastener layers 60. As shown in FIG. 15, the charger support 200 maintains a distance D between the fastener layer 60 and the fastener 104, thereby preventing the fastener layer 60 and fastener 104 from mating with one another and, by doing so, facilitating movement of the IMD charger apparatus relative to garment 50 and IMD. The smooth and curved shape of the charger support bottom end 214 further facilitates such movement. The IMD charger apparatus 10 may then be moved laterally in any direction as it slides along the garment 50 until the IMD charger 100 generates an audible, visible and/or tactile indication that the IMD charger primary charging coil 124 is aligned with IMD secondary charging coil 90. After the IMD charger apparatus has been properly positioned and there is charging alignment, the user may apply a downward force, thereby compressing the charger support collapsible portion 204 (FIG. 16), until the IMD charger fastener 104 mates with the garment fastener layer 60. The IMD charger apparatus 10 will remain in this state after the downward force is removed. The accurately positioned IMD charger apparatus 10 may then be used to transfer power to the associated IMD 80 to charge the power source 86.

Figures 22, 23, 24, 25A, 25B:
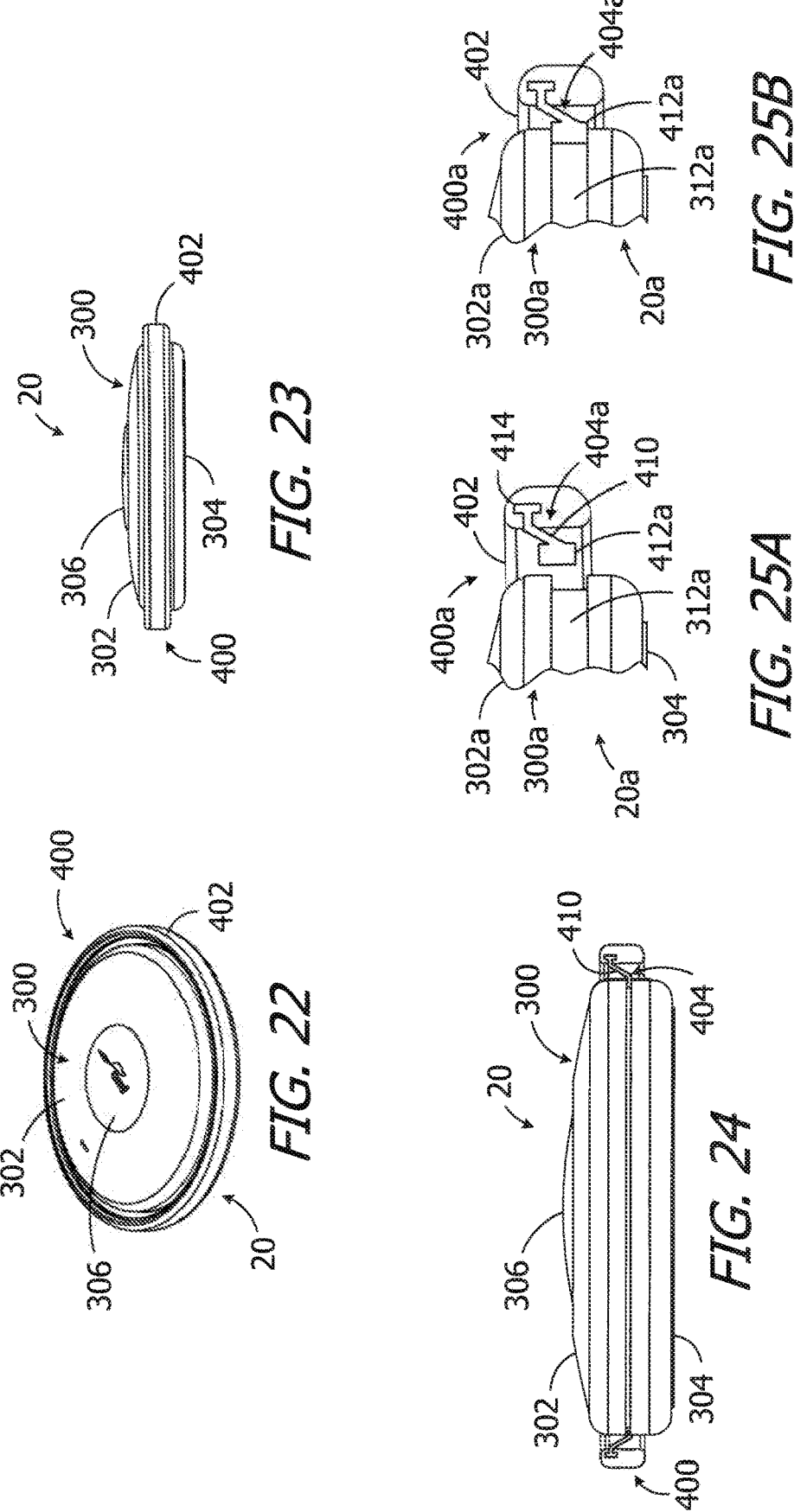
FIG. 22 is a perspective view the IMD charger apparatus illustrated in FIG. 17 in a second state.
FIG. 23 is a side view of the IMD charger apparatus illustrated in FIG. 17 in the second state.
FIG. 24 is a partial section view of the IMD charger apparatus illustrated in FIG. 17 in the second state.
FIG. 25A is a partial section view of a portion of an IMD charger apparatus in accordance with one embodiment of a present invention in a partially assembled state.
FIG. 25B is a partial section view of the IMD charger apparatus illustrated in FIG. 25A in an assembled state.
Figures 26, 27, 28, 29:
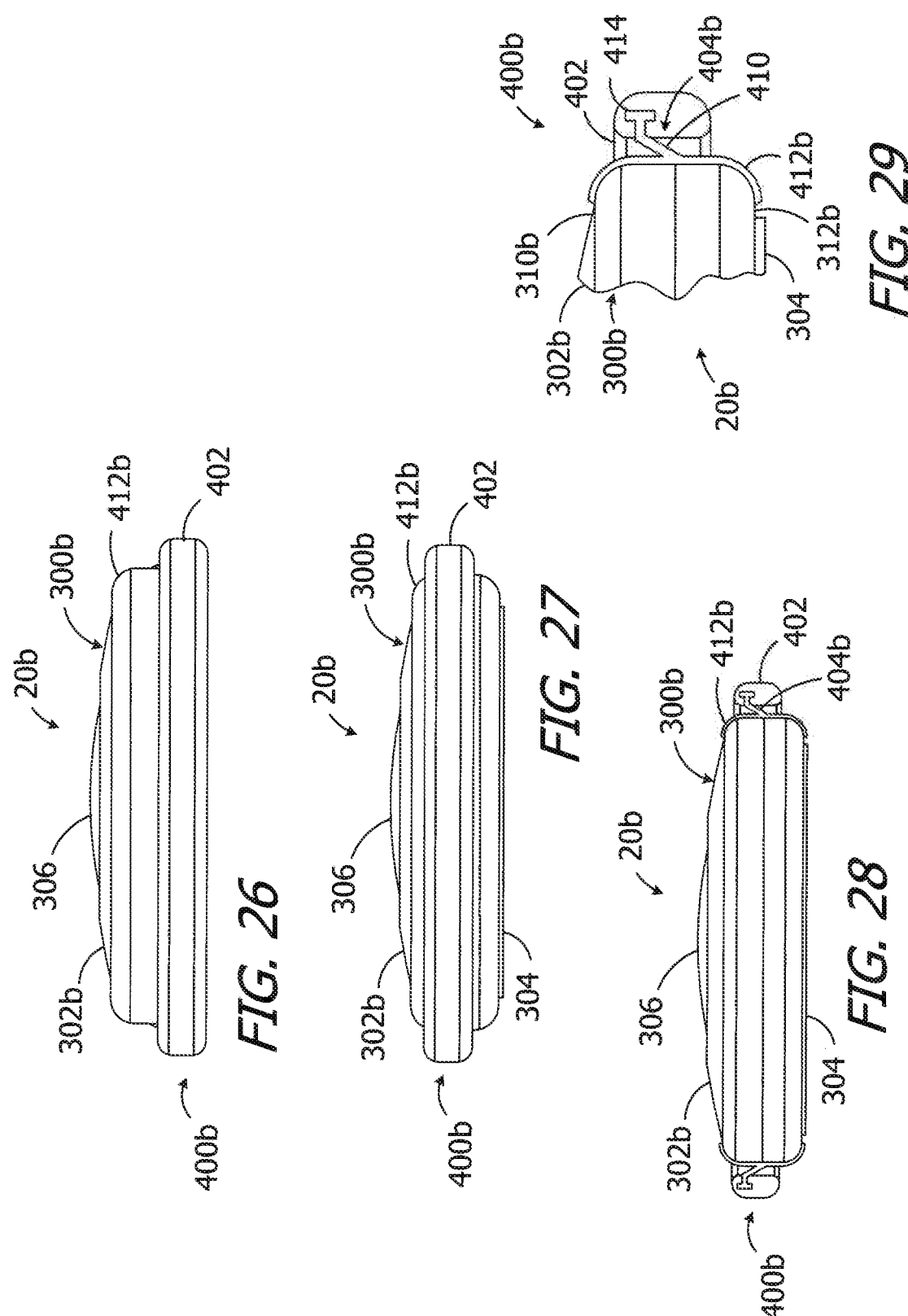
FIG. 26 is a side view of an IMD charger apparatus in accordance with one embodiment of a present invention in a first state.
FIG. 27 is a side view of the IMD charger apparatus illustrated in FIG. 26 in the second state.
FIG. 28 is a partial section view of the IMD charger apparatus illustrated in FIG. 26 in the second state.
FIG. 29 is an enlarged view of a portion of FIG. 28.

Another exemplary IMD charger apparatus, which is generally represented by reference numeral 20 in FIGS. 17-24, includes an IMD charger 300 and a charger support 400 that is mounted to the IMD charger and is movable between a first (or "lowered") state (FIGS. 17-21) and a second (or "raised") state (FIGS. 22-24). Here too, the charger support 400 allows the IMD charger 300 to move laterally relative to the associated IMD during the positioning process and to thereafter be pressed against the recipient or a wearable article on the recipient. The IMD charger apparatus 20 may also form part of a system similar to the system illustrated in FIG. 14 that also includes the garment 50 or other wearable article.

Referring more specifically to FIGS. 17-21, the exemplary IMD charger 300 includes a housing 302, a fastener 304 that is associated with the bottom of the housing, and a user interface 306 such as a power button. The internal components of the IMD charger 300 are the same as those described above with reference to FIG. 13A. The exemplary fastener 304 may be an adhesive dot (as shown) or any of the other fasteners described above. The housing 302 may be a two-part structure that includes top and bottom portions 308 and 310 that are secured to one another during the assembly process. The exemplary charger support 400 includes a movable ring 402 and a hinge 404. The exemplary movable ring 402 is generally annular in shape and has a smooth, semi-circular or otherwise curved bottom end 406. The hinge 404 in the exemplary implementation is permanently mounted to the IMD housing 302 and to the movable ring 402. To that end, hinge 404 may include a hinge arm 410, a first anchor 412 that is permanently secured to the IMD housing 302, and a second anchor 414 that is permanently secured to the movable ring 402. The IMD charger top and bottom housing portions 308 and 310 include internal slots 312 and 314 that together form a receptacle for the anchor 412, while the anchor 414 is molded into the movable ring 402. Suitable materials for the ring 402 and hinge 404 include, but are not limited to, flexible biocompatible materials such as silicone, polycarbonate, polyurethane, polysulfone, and polyamide. The IMD charger housing bottom portion 310 also has a recess 316 for the fastener 304.

Figures 17, 18, 19, 20, 21:
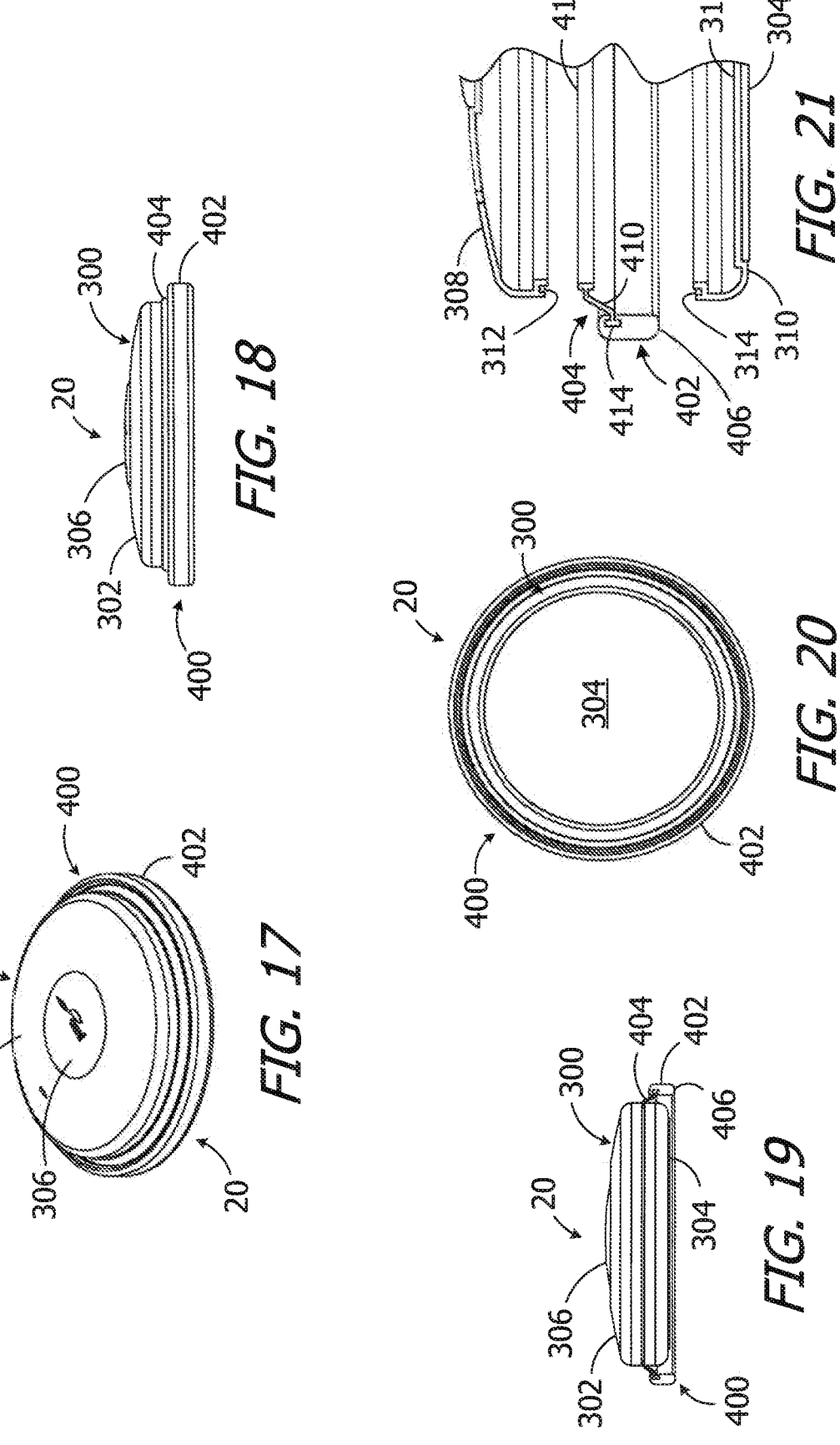
FIG. 17 is a perspective view of an IMD charger apparatus in accordance with one embodiment of a present invention in a first state.
FIG. 18 is a side view of the IMD charger apparatus illustrated in FIG. 17.
FIG. 19 is a partial section view of the IMD charger apparatus illustrated in FIG. 17.
FIG. 20 is a bottom view of the IMD charger apparatus illustrated in FIG. 17.
FIG. 21 is an exploded section view of a portion of the IMD charger apparatus illustrated in FIG. 17.

Referring more specifically to FIGS. 18 and 19, the configurations of the IMD charger 300 and the charger support 400 are such that the curved bottom end 406 of the ring 402 is located below the fastener 304 when the charger support is in the first (or "lowered") state. As such, the fastener 304 will not prevent or interfere with movement of the IMD charger apparatus 20 when the IMD charger apparatus is in contact with, and is sliding over, a wearable article or skin in a manner similar to that described above with reference to FIGS. 15 and 16. After the charging coils have been aligned, the charger support 400 may be moved into the second (or "raised") state illustrated in FIGS. 22-24 by pressing down on the IMD charger 300, which results in a corresponding upward force on the ring 402 that causes the hinge arm 410 to pivot about the anchor 414 (FIG. 21) as the ring moves upwardly. Such movement of the ring 402 allows the fastener to secure the IMD charger apparatus 20 to, for example, the skin of the IMD recipient or a wearable article.

It should also be noted here that, in other implementations, IMD charger apparatus similar to IMD charger apparatus 20 may be configured in such a manner that the charger support is removable. Referring for example to FIGS. 25A and 25B, the exemplary IMD charger apparatus 20a is substantially similar to IMD charger apparatus 20 and similar elements are represented by similar reference numerals. For example, the IMD charger apparatus 20a includes an IMD charger 300a and a charger support 400a that is mounted to the IMD charger and is movable between a first (or "lowered") state and a second (or "raised") state. The IMD charger 300a includes a housing 302a and a fastener 304, while the charger support 400a includes a ring 402 and a hinge 404a. Here, however, the IMD charger housing 302a has an outer slot 312a that extends around the perimeter of the outer surface of the housing, and the hinge 404a includes an anchor 412a that is sized and shaped to fit into the outer slot. The inner diameter of the hinge anchor 412a in an unstretched state may be slightly less than the inner diameter of the outer slot 312a so that there is tension on the hinge anchor when the hinge anchor is located within the outer slot.

The exemplary charger support 400a may mounted onto the IMD charger 300a by stretching the charger support as shown in FIG. 25A and then releasing the charger support in such a manner that the anchor 412a enters the housing slot 312a in the manner illustrated in FIG. 25B. The charger support 400a may be removed from the IMD charger 300a, without disassembly or destruction of the IMD charger or the charger support, by stretching the charger support in the manner illustrated in FIG. 25A so that the anchor 412a exits the housing slot 312a. The charger support 400a may then be pulled over and away from the IMD charger 300a.

In other implementations, charger supports may be configured to be mounted onto a conventional IMD charger to form an IMD charger apparatus in accordance with the present inventions. Referring to FIGS. 26-29, the exemplary IMD charger apparatus 20b is substantially similar to IMD charger apparatus 20 and similar elements are represented by similar reference numerals. For example, the IMD charger apparatus 20b includes an IMD charger 300b and a charger support 400b that may be mounted to the IMD charger and is movable between a first (or "lowered") state and a second (or "raised") state.

The IMD charger 300b includes a housing 302b, a fastener 304 and user interface 306 such as a power button, while the charger support 400b includes a ring 402 and a hinge 404b. Here, however, the IMD charger housing 302b does not have structural elements that are specifically configured to have a charger support anchored thereto. The IMD charger housing 302b does not, for example, have one or more internal slots (such as 312 and 314 in FIG. 21) or an external slot (such as slot 312a in FIGS. 25A and 25B), and the hinge 404b does not include an anchor (such as anchor 412 in FIG. 21 or anchor 412a in FIG. 25A) that is sized and shaped to fit into such a slot. Instead, the hinge 404b includes an anchor 414b that is configured to extend around the perimeter of the IMD charger housing 302b, and over small portions of the top and bottom surfaces 310b and 312b of the housing, when stretched. The inner diameter of the hinge anchor 412b in an unstretched state may be slightly less than the outer diameter of the IMD charter housing 302*b* so that there is tension on the hinge anchor when the hinge anchor is on the housing.

The exemplary charger support 400*b* may mounted onto the IMD charger 300*b* by stretching the charger support in a manner similar to that described above with reference to FIG. 25A and then releasing the charger support. The charger support 400*b* may be removed from the IMD charger 300*b*, without disassembly or destruction of the IMD charger or the charger support, by stretching the charger support in the same manner so that a portion of the anchor 412*b* may be pulled over and away from the IMD charger 300*b*.

Although the inventions disclosed herein have been described in terms of the preferred embodiments above, numerous modifications and/or additions to the above-described preferred embodiments would be readily apparent to one skilled in the art. It is intended that the scope of the present inventions extend to all such modifications and/or additions. The inventions include any and all combinations of the elements from the various embodiments disclosed in the specification. The scope of the present inventions is limited solely by the claims set forth below.

We claim:

1. An implantable medical device (IMD) charger apparatus for use with an IMD that is implanted in a recipient, the IMD charger apparatus comprising:
an IMD charger including a housing defining a bottom surface, a primary coil located within the housing, and a fastener on the bottom surface of the housing; and
a charger support, mounted on the IMD charger, including a bottom surface, and movable between a first state and a second state;
wherein the IMD charger and the charger support are respectively configured such that the IMD charger fastener is above the charger support bottom surface when the charger support is in the first state and the IMD charger fastener is at or below the charger support bottom surface when the charger support is in the second state.

2. The IMD charger apparatus claimed in claim 1, wherein the charger support is biased to the first state.

3. The IMD charger apparatus claimed in claim 1, wherein the charger support includes a base portion that is mounted to the IMD charger and a collapsible portion, with the bottom surface, that is configured to collapse as the charger support moves from the first state to the second state.

4. The IMD charger apparatus claimed in claim 3, wherein the IMD charger housing includes a slot; and
the charger support base portion includes a surface that is configured to be received by the slot.

5. The IMD charger apparatus claimed in claim 3, wherein the charger support collapsible portion comprises a pleated portion.

6. The IMD charger apparatus claimed in claim 1, wherein the charger support includes a ring with the bottom surface and a hinge that is connected to the ring, mounted to the IMD charger and configured to allow the ring to move from the first state to the second state.

7. The IMD charger apparatus claimed in claim 1, wherein the bottom surface comprises a smooth and curved bottom surface.

8. The IMD charger apparatus claimed in claim 1, wherein the charger support is removably mounted to the IMD charger housing.

9. The IMD charger apparatus claimed in claim 1, wherein the charger support is permanently mounted to the IMD charger housing.

10. The IMD charger apparatus claimed in claim 1, further comprising:
a controller located within the IMD charger housing; and
a power source, located within the IMD charger housing, operably connected to the controller and to the primary coil.

11. The IMD charger apparatus claimed in claim 1, wherein
the IMD charger includes coil module that includes the fastener and the primary coil and an electronics module, operably connected to the coil module, that includes a user interface, a controller, and a power source.

12. The IMD charger apparatus claimed in claim 1, further comprising:
a wearable article including a fastener configured to mate with the IMD charger fastener.

13. The IMD charger apparatus claimed in claim 1, further comprising:
the fastener is selected from the group consisting of a hook and loop fastener hook portion, a hook and loop fastener loop portion, an adhesive tape, a portion of a snap, and a button.

14. A method of securing an implantable medical device (IMD) charger to an IMD recipient, the method comprising:
positioning an IMD charger apparatus including an IMD charger with a housing defining a bottom surface, a primary coil located within the housing and a fastener on the bottom surface, and a charger support with a bottom surface, on either the IMD recipient or a wearable article worn by the IMD recipient in such a manner that the bottom surface of the charger support is in contact with the IMD recipient or the wearable article and the fastener of the IMD charger is spaced apart from the contacted IMD recipient or the wearable article;
moving the IMD charger into charging alignment with an IMD within the IMD recipient while the charger support is in contact with the IMD recipient or the wearable article; and
after the IMD charger has been moved into charging alignment with the IMD, pressing the IMD charger downward until the fastener of the IMD charger is in contact with the IMD recipient or the wearable article.

15. The method claimed in claim 14, wherein
positioning step comprises positioning the IMD charger apparatus on the wearable article.

16. The method claimed in claim 14, wherein
positioning step comprises positioning the IMD charger apparatus on the IMD recipient.

17. The method claimed in claim 14, wherein
the fastener is selected from the group consisting of a hook and loop fastener hook portion, a hook and loop fastener loop portion, an adhesive tape, a portion of a snap, and a button.

18. The method claimed in claim 14, further comprising:
charging a power source of the implanted IMD with the IMD charger.

* * * * *